United States Patent [19]

Yamamuro et al.

[11] 4,448,878
[45] May 15, 1984

[54] SILVER HALIDE PHOTOGRAPHIC LIGHT-SENSITIVE MATERIALS

[75] Inventors: Kiyohiko Yamamuro; Shigeo Hirano; Yasuo Iwasa, all of Kanagawa, Japan

[73] Assignee: Fuji Photo Film Co., Ltd., Kanagawa, Japan

[21] Appl. No.: 441,208

[22] Filed: Nov. 12, 1982

[30] Foreign Application Priority Data

Nov. 13, 1981 [JP] Japan .................................. 56-181994
Dec. 2, 1981 [JP] Japan .................................. 56-193832

[51] Int. Cl.³ .............................................. G03C 1/34
[52] U.S. Cl. .................................... 430/507; 430/505; 430/600; 430/611; 430/551; 430/614
[58] Field of Search ............... 430/611, 600, 551, 614, 430/505, 507

[56] References Cited

U.S. PATENT DOCUMENTS 2,403,927 7/1946 Kendall ................................ 430/611
3,397,987 8/1968 Luckey et al. ...................... 430/611
3,708,303 1/1973 Salesin ................................. 430/611

Primary Examiner—Won H. Louie, Jr.
Attorney, Agent, or Firm—Sughrue, Mion, Zinn, Macpeak and Seas

[57] ABSTRACT

A silver halide photographic light-sensitive material is disclosed. The material contains at least one member of the compounds represented by the general formula:

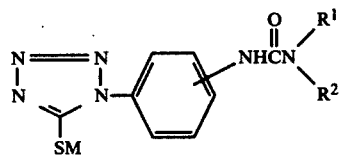

(wherein the symbols are the same as described in the appended claims). In this silver halide photographic light-sensitive material, variations in photographic performance are prevented during the storage thereof and, further, the occurrence of fog is prevented without causing a reduction in sensitivity.

12 Claims, No Drawings

SILVER HALIDE PHOTOGRAPHIC LIGHT-SENSITIVE MATERIALS

FIELD OF THE INVENTION

The present invention relates to silver halide photographic light-sensitive materials, and particularly, to silver halide photographic light-sensitive materials in which variations in photographic performance during the storage thereof are prevented and, further, in which the occurrence of fog is prevented without causing the reduction of sensitivity involved in restraining development.

BACKGROUND OF THE INVENTION

Silver halide photographic light-sensitive materials (hereinafter referred to merely as "light-sensitive materials") tend to be easily varied in photographic performance (e.g., sensitivity, gradation, and in particular, fog) during the storage thereof. Although it is impossible to completely avoid such variations in photographic performance with the lapse of time, it is desirable to reduce them as much as possible. Therefore, a number of investigations have heretofore been made for that purpose.

It is known that in order to prevent variations in photographic performance, particularly the occurrence of fog involved in storage or development, heterocyclic compounds such as 1-phenyl-5-mercaptotetrazoles (as described in Belgian Pat. No. 671,402, U.S. Pat. Nos. 3,295,976, 3,376,310, 3,615,616, 3,071,465, 3,420,664 and 2,403,927, Japanese patent application (OPI) No. 37436/75 (the term "OPI" as used herein refers to a "published unexamined Japanese patent application"), etc.), benzotriazoles (as described in British Pat. Nos. 919,061 and 768,438, U.S. Pat. Nos. 3,157,509 and 3,082,088, German Pat. No. 617,712, etc.), benzimidazoles (as described in U.S. Pat. Nos. 3,137,578, 3,148,066 and 3,511,663, British Pat. Nos. 271,475, 1,344,548, 3,148,066 and 3,511,663, German Pat. Nos. 708,424, 635,769 and 2,205,539, etc.), and indazoles (as described in U.S. Pat. Nos. 3,106,467, 3,420,670, 1,763,990 and 2,271,229, etc.) are incorporated in light-sensitive materials, or added to processing solutions. These compounds, however, have disadvantages in that their effect with respect to inhibiting the increase of fog during the storage is insufficient and they give rise to a reduction in sensitivity.

In color light-sensitive materials, particularly those for picture-taking, the amount of silver salt used is large and, further, colloidal silver is used in a yellow filter layer and an antihalation layer. This increases the time required for bleaching, which presents an obstacle with respect to increasing the processing speed. Compounds having a high fog-preventing effect, e.g., 1-(amidophenyl)-5-mercaptotetrazole, among the known antifoggants easily form stable salts in combination with silver and, therefore, they retard the removal of silver during a bleaching step, further decreasing the processing speed. This tendency is prominent particularly when bleaching agents having a low bleaching power, for example, persulfates, are used. Therefore, there is a need for stabilizers which are capable of preventing variations in photographic performance during storage without reducing desilvering properties. However, none of the conventionally known compounds meet these needs.

SUMMARY OF THE INVENTION

An object of the invention is to provide light-sensitive materials in which variations in photographic performance, particularly the occurrence of fog, during the storage thereof are prevented.

Another object of the invention is to provide light-sensitive materials containing compounds which make it possible to prevent the occurrence of fog without causing the reduction of sensitivity involved in restraining development, and to attain a substantial increase in sensitivity.

A further object of the invention is to provide color light-sensitive materials in which the occurrence of fog is prevented by compounds which do not obstruct desilvering properties during the bleaching step.

Still another object of the invention is to provide color light-sensitive materials in which the occurrence of fog is prevented, and desilvering is rapidly completed when bleached with bleaching agents having a low bleaching power, particularly with persulfates.

It has been found that these objects are attained by adding to light-sensitive materials at least one member of the compounds represented by the general formula (I):

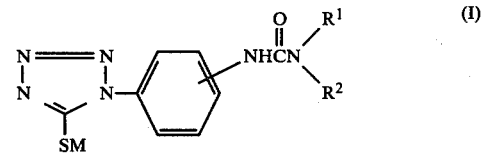

wherein M is hydrogen, an alkali metal atom, or a quaternary ammonium group; and $R^1$ and $R^2$ are each hydrogen, a substituted or unsubstituted aliphatic group, or a substituted or unsubstituted aromatic group, and they may be the same or different and may combine together to form a ring.

DETAILED DESCRIPTION OF THE INVENTION

In general, compounds capable of forming stable insoluble silver salts have a great fog-inhibiting ability, but contrarily tend to have reduced desilvering properties. Unexpectedly and surprisingly the compounds as used herein have a great fog-preventing ability and, at the same time, have excellent desilvering properties.

The compounds as used herein will hereinafter be explained in detail.

In the general formula (I), examples of alkali metal atom represented by M include $Li^\oplus$, $Na^\oplus$, and $K^\oplus$. Examples of quaternary ammonium group include $H_4N^\oplus$, $(CH_3)_4N^\oplus$, $(C_4H_9)_4N^\oplus$, $n-C_{12}H_{25}(CH_3)_3N^\oplus$, $n-C_{16}H_{33}(CH_3)_3N^\oplus$ and

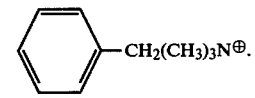

Atoms of M are preferably hydrogen or the alkali metal atoms.

Aliphatic groups of $R^1$ and $R^2$ are preferably alkyl groups and alkenyl groups, the number of carbon atoms being 18 or less, such as a methyl group, an ethyl group, an n-propyl group, an n-butyl group, a tert-butyl group, an n-pentyl group, an n-hexyl group, a cyclohexyl group, an n-octyl group, an n-dodecyl group, an n-octadecyl group, and an allyl group.

Aromatic groups of $R^1$ and $R^2$ are preferably aryl groups containing from 6 to 20 carbon atoms, such as a phenyl group and a naphthyl group.

The ring formed by $R^1$ and $R^2$ is a ring containing from 2 to 10 carbon atoms, which may contain O, N or S in the ring thereof. Examples of ring include $-(CH_2)_4-$, $-(CH_2)_5-$, $-(CH_2)_6-$, $-CH_2CH_2OCH_2CH_2-$ and $-CH_2CH_2N(CH_3)CH_2CH_2-$.

Examples of substituents in $R^1$ and $R^2$ include an alkoxy group (e.g., a methoxy group and an ethoxy group), halogen (e.g., chlorine and bromine), an alkyl group (e.g., a methyl group and an ethyl group), a phenyl group, an alkoxycarbonyl group (e.g., an ethoxycarbonyl group), an acyl group (e.g., an acetyl group), an acyloxy group (e.g., an acetyloxy group), a cyano group, a nitro group, an alkylthio group (e.g., a methylthio group), an amido group (e.g., an acetamido group), and a sulfonamido group (e.g., a methanesulfonamido group).

At least one of $R^1$ and $R^2$ is preferably an alkyl group containing from 1 to 6 carbon atoms and a phenyl group, of which a methyl group, an ethyl group, an n-propyl group, an n-butyl group and particularly preferably an n-pentyl group.

Typical examples of the compounds represented by the general formula (I) are shown below, although the invention is not limited thereto.

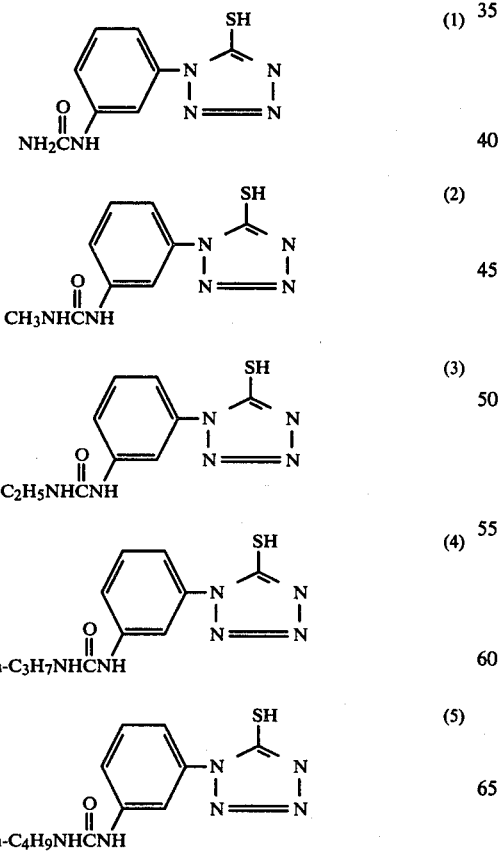

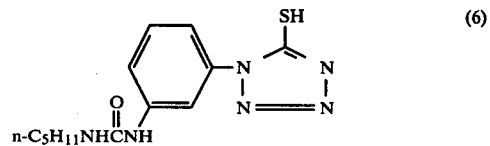

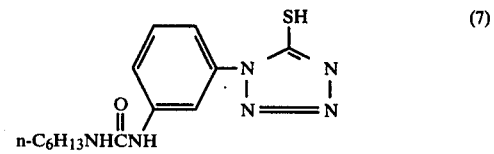

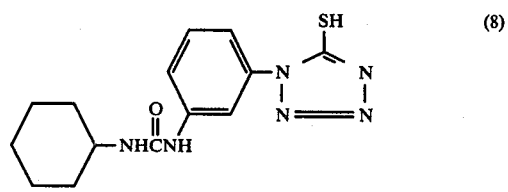

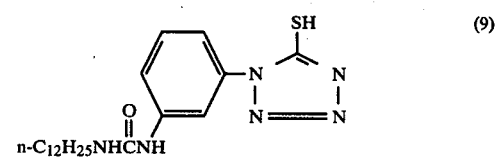

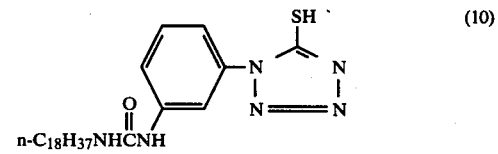

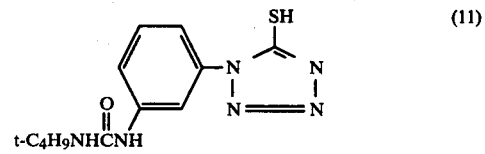

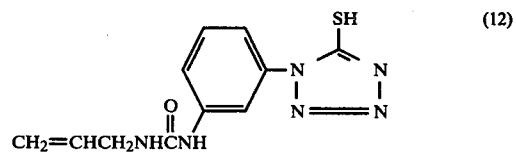

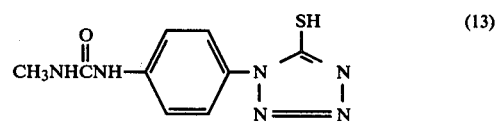

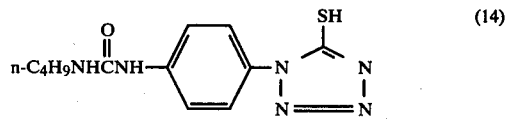

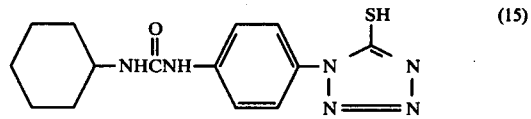

-continued
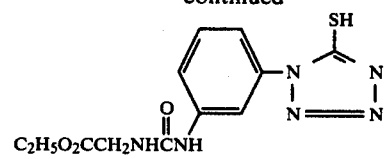 (16)
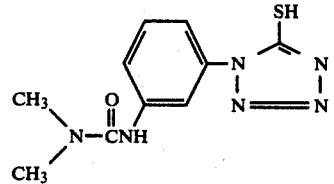 (17)
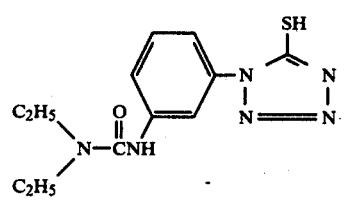 (18)
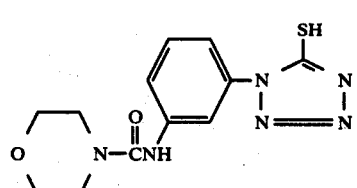 (19)
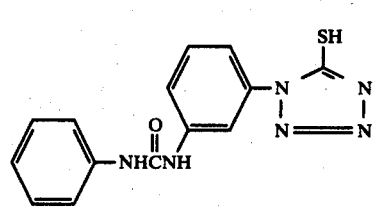 (20)
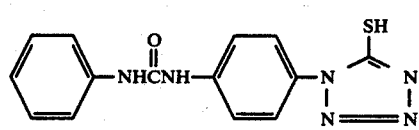 (21)
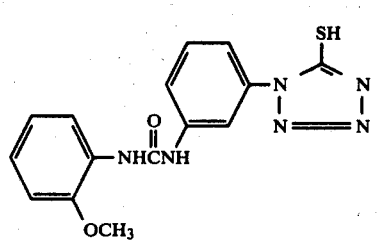 (22)
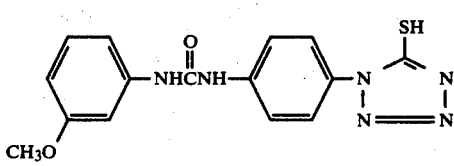 (23)
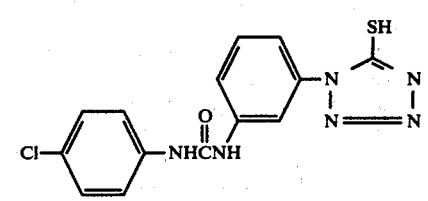 (24)
-continued
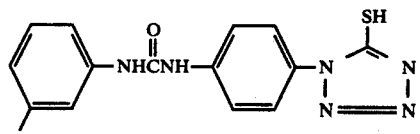 (25)
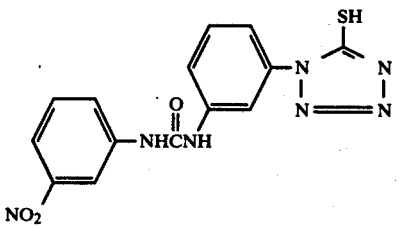 (26)
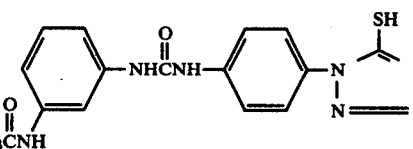 (27)
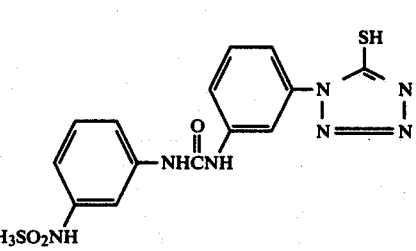 (28)
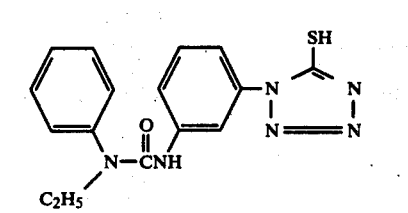 (29)
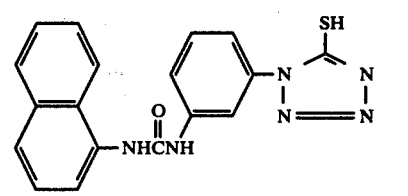 (30)
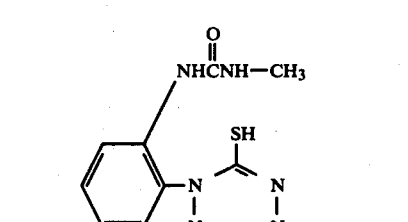 (31)

-continued

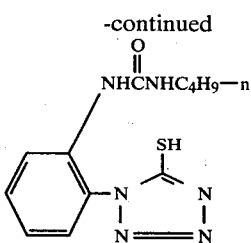
(32)

In general, these compounds can be synthesized by reacting amino-substituted 1-phenyl-5-mercaptotetrazole, which is prepared by hydrolyzing the amido group of amido-substituted 1-phenyl-5-mercaptotetrazole with a strong acid, e.g., hydrochloric acid, said amido-substituted 1-phenyl-5-mercaptotetrazole being described in Japanese Patent Application (OPI) Nos. 37436/65 and 3231/76, and U.S. Pat. Nos. 3,295,976 and 3,376,310 (incorporated herein by reference to disclose these methods of preparation), with suitable isoaminic acid ester or N,N-di-substituted carbamoyl chloride.

Hereinafter, typical synthesizing methods are described.

Synthesis of Compound (5)

In 450 ml of ethanol was dispersed 150 g (0.51 mol) of 1-(3-hexaneamidophenyl)-5-mercaptotetrazole, to which 300 ml of concentrated hydrochloric acid was added while stirring at room temperature. They were reacted at room temperature for 3 hours and then cooled with ice to precipitate crystals. These crystals were collected and washed with acetone to obtain 110 g of 1-(3-aminophenyl)-5-mercaptotetrazole hydrochloride. This amine hydrochloride was dispersed in 750 ml of acetonitrile, and after addition of 485 ml of triethylamine, 125 g of butyl isocyanate was added dropwise at room temperature. They were reacted at room temperature for 6 hours. At the end of the time, 2,200 ml of water was added, and the resulting mixture was adjusted to pH 2 by the addition of hydrochloric acid. The thus-precipitated crystals were collected and recrystallized from ethanol to obtain 69 g (yield: 46%) of the desired product, m.p. 171°–172° C. (decomposition).

Synthesis of Compound (18)

A mixture of 23 g of 1-(3-aminophenyl)-5-mercaptotetrazole and 32 g of pyridine was dispersed in 220 ml of acetonitrile, and 16 g of N,N-diethylcarbamoyl chloride was added dropwise thereto. The mixture was then heated to reflux for 1.5 hours. At the end of the time, 200 ml of water was added, and extraction was performed with ethyl acetate. After concentration, recrystallization was performed using 250 ml of acetonitrile to obtain 15 g (yield: 51%) of the desired product, m.p. 184°–185° C. (decomposition).

The other compounds can be synthesized in the same manner as above.

The compound of the invention is incorporated into at least one layer constituting light-sensitive materials. The amount of the compound added should be appropriately changed depending on the type of the compound and the layer into which the compound is to be incorporated, and cannot be determined unconditionally. In general, it has been found that the variations in photographic performance during the storage, particularly the occurrence of fog can be prevented by adding the compound in an amount of from $10^{-8}$ to $10^{-2}$ mol per mol of silver halide when it is incorporated into a silver halide emulsion layer, or by adding the compound in an amount of from $10^{-4}$ to 1 mol per mol of silver when it is incorporated into a colloid silver layer. It is more preferred that the compound is added in an amount of from $10^{-6}$ to $10^{-3}$ mol per mol of silver halide; i.e., from $10^{-3}$ to $10^{-1}$ mol per mol of silver.

The compound of the invention can be incorporated into any of the usual auxiliary layers constituting light-sensitive material, such as a protective film layer, a subbing layer, an intermediate layer, a yellow filter layer, and an antihalation layer, as well as into a silver halide emulsion layer. It is preferred for the compound to be incorporated into a layer containing silver halide or colloid silver. In particular, the incorporation of the compound of the invention into the colloid silver-containing layers, such as a yellow filter layer and an antihalation layer, of color light-sensitive material produces the great advantages that the increase with time of fog in the adjacent layer caused by the colloid silver (the increment of fog caused by the action as physical development nuclei of colloid silver diffused into the adjacent layer) can be prevented without decreasing sensitivity, and that the desilvering properties of the colloid silver are not obstructed.

In the photographic emulsion layer of the light-sensitive material of the invention, any of silver bromide, silver iodobromide, silver iodochlorobromide, silver chlorobromide, and silver chloride can be used as silver halide. The mean grain size of silver halide particles contained in the photographic emulsion is not critical, but it is preferably 3μ or less. The mean grain size as used herein is determined by calculating from projected areas with the particle diameter when the particles are spherical or are similar to spheres, or the edge length when the particles are cubic as the grain size. The grain size distribution may be narrow or broad.

Silver halide particles contained in the photographic emulsion may have a regular crystal form, for example, a cubic crystal form or an octahedral crystal form, or an irregular crystal form, for example, a spherical crystal form or a plate-like crystal form, or may have a composite crystal form. In addition, they may be a mixture of particles having various crystal forms.

These silver halide particles may be composed of a surface layer and an interior which are different in phase from each other, or have a homogeneous phase. It is possible to use either particles in which a latent image is formed mainly in the surface thereof, or particles in which a latent image is formed mainly in the interior thereof.

Photographic emulsions as used herein can be prepared by methods as described in, for example, P. Glafkides, *Chimie et Physique Photographique*, Paul Montel (1976), G. F. Duffin, *Photographic Emulsion Chemistry*, The Focal Press (1966), and V. L. Zelikman et al., *Making and Coating Photographic Emulsion*, The Focal Press (1964). That is, any of an acidic process, a neutral process, an ammonia process, and so forth can be used. In reacting soluble silver salts and soluble halogen salts, any of a single jet process, a double jet process, and a combination thereof can be used.

In addition, there can be used a method in which particles are formed in the presence of an excess of silver ions (so-called reverse mixing process). An example of a useful type of double jet process is a method in which the pAg of a liquid phase where silver halide is formed in maintained at a definite level, i.e., the so-called controlled double jet process. In accordance with this process, a silver halide emulsion can be obtained in which the crystal form is regular and the grain size is nearly uniform.

Two or more types of silver halide emulsions which have been separately prepared can be used in combination with each other.

The formation or physical ripening of silver halide particles may be performed in the presence of a cadmium salt, a zinc salt, a lead salt, a thallium salt, an iridium salt or its complex salt, a rhodium salt or its complex salt, an iron salt or its complex salt, and the like.

Either a negative type emulsion forming a surface latent image or a direct reversal type emulsion can be used in the invention. The latter direct reversion type emulsion includes an internal latent image type emulsion and a previously fogged direct reversal type emulsion.

Internal latent image type silver halide emulsions which can be advantageously used in the invention include a conversion type emulsion, a core/shell type emulsion, and an emulsion with different metals incorporated therein, as described in, for example, U.S. Pat. Nos. 2,592,250, 3,206,313, 3,447,927, 3,761,276 and 3,935,014.

Typical examples of nucleating agents for use in the preparation of emulsions of that type are hydrazines described in U.S. Pat. Nos. 2,588,982 and 2,563,785, hydrazides and hydrazones described in U.S. Pat. No. 3,227,552, quaternary salt compounds described in British Pat. No. 1,283,835, Japanese Patent Publication No. 38164/74, U.S. Pat. Nos. 3,734,738, 3,719,494 and 3,615,615, sensitizing dyes containing therein a nucleating substituent described in U.S. Pat. No. 3,718,470, and acylhydrazinophenylthiourea compounds described in U.S. Pat. Nos. 4,030,925 and 4,031,127.

These silver halide emulsions are usually chemically sensitized although they may be used as so-called primitive emulsions without application of chemical sensitization. This chemical sensitization can be performed by the methods described in the above-described references of P. Glafkides and V. L. Zelikman et al., and H. Frieser ed., *Die Grundlagen der Photographischen Prozesse mit Silverhalogeniden*, Akademische Verlagsgesellschaft (1968). That is, a sulfur sensitization method in which a compound containing sulfur capable of reacting with silver ions or an active gelatin is used, a reduction sensitization method in which a reducing substance is used, and a noble metal sensitization method in which noble metal compounds, e.g., gold, is used can be used alone or in combination with each other.

Sulfur sensitizing agents which can be used include thiosulfates, thioureas, thiazoles, and rhodanines. Representative examples are described in U.S. Pat. Nos. 1,574,944, 2,410,689, 2,278,947, 2,728,668 and 3,656,955. Reducing sensitizing agents which can be used include tin (II) salts, amines, hydrazine derivatives, formamidinsulfinic acid, and silane compounds. Representative examples are described in U.S. Pat. Nos. 2,487,850, 2,419,974, 2,518,698, 2,983,609, 2,983,610 and 2,695,637. For noble metal sensitization, complex salts of Group VIII metals, e.g., platinum, iridium, and palladium, of the Periodic Table, as well as gold complex salts can be used. Representative examples are described in U.S. Pat. Nos. 2,399,083, 2,448,060, British Pat. No. 618,061, etc.

Photographic emulsions may be subjected to spectral sensitization using, for example, methine dyes. Other dyes which can be used include cyanine dyes, merocyanine dyes, complex cyanine dyes, complex merocyanine dyes, holopolar cyanine dyes, hemicyanine dyes, styryl dyes, and hemioxonol dyes. Particularly useful dyes are those belonging to the cyanine dyes, merocyanine dyes, and complex merocyanine dyes.

Useful sensitizing dyes are described in, for example, German Pat. No. 929,080, U.S. Pat. Nos. 2,231,658, 2,493,748, 2,503,776, 2,519,001, 2,912,329, 3,655,394, 3,656,959, 3,672,897 and 3,694,217, British Pat. No. 1,242,588 and Japanese Patent Publication No. 14030/69.

In addition to the layer of the light-sensitive silver halide emulsion as described above, a layer of a substantially light-insensitive fine particle silver halide emulsion may be provided in order to improve granularity and sharpness, and for other purposes. This substantially light-insensitive fine particle emulsion layer can be provided either on the top of the light-sensitive silver halide emulsion layer, or between the light-sensitive silver halide emulsion layer and a colloid silver layer (i.e., a yellow filter layer or an antihalation layer).

For the purposes of increasing sensitivity and contrast, and of accelerating development, polyalkylene oxides or their ether, ester, amine or like derivatives, thioether compounds, thiomorpholines, quaternary ammonium salt compounds, urethane derivatives, urea derivatives, imidazole derivatives, 3-pyrazolidones, etc. may be incorporated into the light-sensitive material of the invention. Typical examples are described in U.S. Pat. Nos. 2,400,532, 2,423,549, 2,716,062, 3,617,280, 3,772,021, 3,808,003, etc.

Gelatin can be advantageously used as a binder in the preparation of the photographic emulsion layer of other constitutive layers, but other hydrophilic colloids can be used. For example, a wide variety of synthetic hydrophilic polymeric substances, such as gelatin derivatives, graft polymers of gelatin and other polymers, proteins, e.g., albumin and casein, cellulose derivatives, e.g., hydroxyethyl cellulose, carboxymethyl cellulose, and cellulose sulfuric acid esters, sugar derivatives, e.g., sodium alginate and starch derivatives, and homopolymers or copolymers, e.g., polyvinyl alcohol, polyvinyl alcohol partial acetal, poly-N-vinylpyrrolidone, polyacrylic acid, polymethacrylic acid, polyacrylamide, polyvinyl imidazole, and polyvinyl pyrazole, can be used.

Examples of useful gelatins include acid-processed gelatin and enzyme-processed gelatin as described in *Bull. Soc. Sci. Phot. Japan*, No. 16, page 30 (1966), as well as lime-processed gelatin. In addition, hydrolyzates and enzyme decomposition products of gelatin can be used. Gelatin derivatives which can be used are those compounds as prepared by reacting gelatin with, for example, acid halides, acid anhydrides, isocyanates, bromoacetic acid, alkanesultones, vinylsulfonamides, maleinimide compounds, polyalkylene oxides, or epoxy compounds. Representative examples are described in, for example, U.S. Pat. Nos. 2,614,928, 3,132,945, 3,186,846 and 3,312,553, British Pat. Nos. 861,414, 1,033,189 and 1,005,784 and Japanese Pat. publication No. 26845/67.

Gelatin graft polymers which can be used include those polymers prepared by grafting on gelatin homopolymers or copolymers of vinyl monomers such as acrylic acid, methacrylic acid or their ester, amido or like derivatives, acrylonitrile, and styrene. Particularly preferred are those graft polymers prepared from gelatin and polymers of, e.g., acrylic acid, methacrylic acid, acrylamide, methacrylamide, or hydroxyalkyl methacrylate, having certain compatibility with gelatin. These polymers are described in, for example, U.S. Pat. Nos. 2,763,625, 2,831,767 and 2,956,884.

Typical synthetic hydrophilic polymerc substances are described in, for example, German Pat. application (OLS) No. 2,312,708, U.S. Pat. Nos. 3,620,751 and 3,879,205, and Japanese patent publication No. 7561/68.

Into the light-sensitive material of the invention can be incorporated various compounds as antifoggants or stabilizers in combination with the compounds represented by the general formula (I). That is, a number of compounds known as antifoggants or stabilizers can be added, including azoles, such as benzothiazolium salts, nitroindazoles, triazoles, benzotriazoles, and benzimidazoles (particularly nitro or halogen-substituted compounds); heterocyclic mercapto compounds, such as mercaptothiazoles, mercaptobenzothiazoles, mercaptobenzimidazoles, mercaptothiadiazoles, mercaptotetrazoles (particularly 1-phenyl-5-mercaptotetrazole), and mercaptopyrimidines; the above-described heterocyclic mercapto compounds containing a water-soluble group, e.g., a carboxy group and a sulfone group; thioketo compounds, such as oxazolinethione; azaindenes, such as tetraazaindenes (particularly 4-hydroxy-substituted (1,3,3a,7)tetraazaindenes); benzenethiosulfonic acids; and benzenesulfinic acid.

In connection with suitable examples of such antifoggants or stabilizers and a method of using them, reference can be made to, for example, U.S. Pat. Nos. 3,954,474, 3,982,947 and 4,021,248 and Japanese patent publication No. 28660/77.

The photographic light-sensitive material of the invention may contain inorganic or organic hardeners in the photographic emulsion or other constitutive layers. For example, chromium salts (e.g., chromium alum and chromium acetate), aldehydes (e.g., formaldehyde, glyoxal, and glutaraldehyde), N-methylol compounds (e.g., dimethylolurea, and methyloldimethylhydantoin), dioxane derivatives (e.g., 2,3-dihydroxydioxane), active vinyl compounds (e.g., 1,3,5-triacryloylhexahydro-s-triazine, and 1,3-vinylsulfonyl-2-propanol), active halogeno compounds (e.g., 2,4-dichloro-6-hydroxy-s-triazine), and mucohalogeno acids (e.g., mucochloric acid and mucophenoxychloric acid) can be used alone or in combination with each other.

Into the photographic emulsion layer or other constitutive layers of the light-sensitive material of the invention may be incorporated various surfactants as coating aids or for the purposes of preventing static charging, improving sliding properties, improving emulsion dispersion, preventing adhesion, or of improving photographic properties (e.g., acceleration of development, high contrast, and sensitization).

Surfactants which can be used in the invention include nonionic surface active agents, such as saponin (steroid-based), alkylene oxide derivatives (e.g., polyethylene glycol, a polyethylene glycol/polypropylene glycol condensate, polyethylene glycol alkyl ethers or polyethylene glycol alkylaryl ethers, polyethylene glycol esters, polyethylene glycol sorbitan esters, polyalkylene glycol alkylamines or amides, and polyethylene-oxide adducts of silicone), glycidol derivatives (e.g., alkenylsuccinic acid polyglyceride, and alkylphenol polyglyceride), aliphatic acid esters of polyvalent alcohols, and alkylesters of sugar; anionic surface active agents containing an acidic group, e.g., a carboxyl group, a sulfo group, a phospho group, a sulfuric acid ester group, and a phosphoric acid ester group, such as alkylcarboxylic acid salts, alkylsulfonic acid salts, alkylbenzenesulfonic acid salts, alkylnaphthalenesulfonic acid salts, alkylsulfuric acid esters, alkylphosphoric acid esters, N-acyl-N-alkyltaurines, sulfosuccinic acid esters, sulfoalkylpolyoxyethylene alkylphenyl ethers, and polyoxyethylene alkylphosphoric acid esters; amphoteric surface active agents, such as amino acids, aminoalkylsulfonic acids, aminoalkylsulfuric acids or phosphoric acid esters, alkylbetaines, and amine oxides; and cationic surface active agents, such as alkylamine salts, aliphatic or aromatic quaternary ammonium salts, heterocyclic quaternary ammonium salts, e.g., pyridinium and imidazolium, and aliphatic or heterocyclic ring-containing phosphonium or sulfonium salts.

The light-sensitive material of the invention may contain color-forming couplers, i.e., compounds capable of forming color through oxidative coupling with aromatic primary amine developers (e.g., phenylenediamine derivatives and aminophenol derivatives) in color development, in the photographic emulsion layer thereof. These color-forming couplers include magenta couplers, such as a 5-pyrazolone coupler, a pyrazolobenzimidazole coupler, a cyanoacetylcumaron coupler, and an open chain acylacetonitrile coupler; yellow couplers, such as acylacetamide couplers (e.g., benzoylacetanilides and pivaloylacetanilides); and cyan couplers, such as a naphthol coupler, and a phenol coupler. Nondiffusion couplers containing therein a hydrophobic group called a ballast group are desirable. These couplers may be 4-equivalent or 2-equivalent relative to silver ion. In addition, colored couplers having the color-correction effect, and compounds releasing a development inhibitor as development proceeds (so-called DIR couplers) can be used. Moreover, colorless DIR coupling compounds providing a colorless coupling reaction product and releasing a development inhibitor, and DIR redox compounds can be added.

Suitable examples of magenta color-forming couplers are described in, for example, U.S. Pat. Nos. 2,600,788, 2,983,608, 3,062,653, 3,127,269, 3,311,476, 3,419,391, 3,519,429, 3,558,319, 3,582,322, 3,615,506, 3,834,908 and 3,891,445, West German Pat. No. 1,810,464, West German patent application (OLS) Nos. 2,408,665, 2,417,945, 2,418,959, and 2,424,467, Japanese patent publication No. 6031/65 and Japanese patent application (OPI) Nos. 20826/76, 13041/75, 58922/77, 129538/74, 74027/74, 159336/75, 42121/77, 74028/74, 60233/75, 26541/76 and 55122/78.

Suitable examples of yellow color-forming couplers are described in, for example, U.S. Pat. Nos. 2,875,057, 3,265,506, 3,408,194, 3,551,155, 3,582,322, 3,725,072 and 3,891,445, West German Pat. No. 1,547,868, West German patent application (OLS) Nos. 2,219,917, 2,261,361 and 2,414,006, British Pat. No. 1,425,020, Japanese patent publication No. 10783/76, and Japanese patent application (OPI) Nos. 26133/72, 73147/73, 102636/76, 6341/75, 123342/75, 130442/75, 21827/76, 87650/75, 82424/77 and 115219/77.

Suitable examples of cyan couplers are described in, for example, U.S. Pat. Nos. 2,369,929, 2,434,272, 2,474,293, 2,521,908, 2,895,826, 3,034,892, 3,311,476, 3,458,315, 3,476,563, 3,583,971, 3,591,383, 3,767,411 and 4,004,929, West German patent application (OLS) Nos. 2,414,830 and 2,454,329, and Japanese patent application (OPI) Nos. 59838/73, 26034/76, 5055/73, 146828/76, 69624/77 and 90932/77.

Colored couplers which can be used are those described in, for example, U.S. Pat. Nos. 3,476,560, 2,521,908 and 3,034,892, Japanese patent publication Nos. 2016/69, 22335/63, 11304/67 and 32461/69, Japanese patent application (OPI) Nos. 26034/76 and 42121/77, and West German patent application (OLS) No. 2,418,959.

DIR couplers which can be used include o-aminoazo type DIR couplers described in U.S. Pat. No. 3,148,062, thioether type DIR couplers described in U.S. Pat. No. 3,227,554, 2-benzotriazole type DIR couplers described in U.S. Pat. No. 3,617,291, 1-benzotriazole type DIR couplers described in West German patent application (OLS) No. 2,414,006, and Japanese patent application (OPI) Nos. 82424/77 and 17627/77, nitrogen-containing hetero ring-substituted acetic acid ester type DIR couplers described in Japanese patent application (OPI) Nos. 30591/75 and 82423/77, 2-equivalent type DIR cyan couplers described in West German patent application (OLS) No. 2,527,652, Japanese patent application (OPI) Nos. 90932/77 and 146828/76, and malonic acid diamide type DIR couplers described in Japanese patent application (OPI) No. 69624/77.

Colorless DIR coupling compounds which can be used include thioether type cyclic colorless DIR compounds described in British Pat. No. 1,423,588, West German patent application (OLS) Nos. 2,405,442, 2,523,705, 2,529,350 and 2,448,063, and U.S. Pat. No. 3,938,996, thioether type chain-like colorless DIR compounds described in U.S. Pat. Nos. 3,632,345 and 3,928,041, benzotriazolyl type colorless DIR compounds described in Japanese patent application (OPI) Nos. 147716/75, 105819/76 and 67628/77, and picolinium type DIR coupling compounds described in Japanese patent application (OPI) No. 72433/76.

DIR redox compounds which can be used include DIR hydroquinones described in U.S. Pat. No. 3,639,417, West German patent application (OLS) No. 2,460,202 and U.S. Pat. No. 3,297,445, and DIR redox type couplers described in Japanese patent application (OPI) No. 57828/77.

The photographic emulsion as used herein can contain dye image-forming compounds for use in so-called diffusion transfer photograhic process (for example, a dye developer, a dye-releasing redox compound, and a DDR coupler). Dye image-forming compounds which can be used are described in, for example, U.S. Pat. Nos. 4,053,312, 4,055,428, 4,076,529, 4,152,153 and 4,135,929, Japanese patent application (OPI) Nos. 149328/78, 104343/76, 46730/78, 130122/79, 3819/78, 12642/81, 16130/81 and 16131/81.

The light-sensitive material of the invention can contain developing agents. For example, the developing agents described in *Research Disclosure*, Vol. 176, page 29, Clause of Developing Agents, can be used.

In the light-sensitive material of the invention, dyes may be incorporated into the photographic emulsion layer or other constitutive layers as filter dyes or for the purposes of, e.g., preventing irradiation. For example, the dyes described in *Research Disclosure*, Vol. 176, page 25, Clause of Absorbing and Filter Dyes, can be used.

In addition, the light-sensitive material of the invention can contain antistatic agents, plasticizers, matting agents, lubricants, ultraviolet absorbers, fluorescent whiteners, air fog-preventing agents, and so forth.

The silver halide emulsion layer and/or other constitutive layers are coated on a support by techniques such as the methods described in *Research Disclosure*, Vol. 176, pages 27 to 28, Clause of Coating Procedures.

Supports which can be used are described in *Research Disclosure*, Vol. 176, page 28, Clause of Supports.

The light-sensitive material of the invention has a wide variety of uses. For example, it can be used as a black-and-white negative material, a black-and-white paper material, a color positive material, a color paper material, a color negative material, a color reversal material (containing or not containing a coupler), a photographic light-sensitive material for use in the production of a printing plate (e.g., a lith film), a light-sensitive material for the display utilizing a cathode ray tube, a light-sensitive material for X-ray recording (particularly, for direct or indirect projection utilizing a screen), a material for use in Colloid Transfer Process (described in, for example, U.S. Pat. No. 2,716,059), a material for use in Silver Salt Diffusion Transfer Process (described in, for example, U.S. Pat. Nos. 2,352,014, 2,543,181, 3,020,155 and 2,861,885), a material for use in a color diffusion transfer process (described in, for example, U.S. Pat. Nos. 3,087,817, 3,185,567, 2,983,606, 3,253,915, 3,227,550, 3,227,551, 3,227,552, 3,415,644, 3,415,645 and 3,415,646 and *Research Disclosure*, Vol. 151, No. 15162, pages 75 to 87 (Nov., 1976)), a material for use in an imbibition transfer process (described in, for example, U.S. Pat. No. 2,882,156), a material for use in a silver dye bleaching process (described in, for example, Friedman, *History of Color Photography*, American Photographic Publishers Co. (1944) (particularly, Chapter 24) and *British Journal of Photography*, Vol. 111, pp. 308–309 (Apr. 7, 1964)), a direct positive light-sensitive material (described in, for example, U.S. Pat. Nos. 2,497,875, 2,588,982, 3,367,778, 3,501,306, 3,501,305, 3,672,900, 3,477,852, 2,717,833, 3,023,102, 3,050,395 and 3,501,307), a heat development type light-sensitive material (described in, for example, U.S. Pat. Nos. 3,152,904, 3,312,550 and 3,148,122, and British Pat. No. 1,110,046), or as a physical development type light-sensitive material (described in, for example, British Pat. Nos. 920,277 and 1,131,238).

The light-sensitive material of the invention is advantageously used particularly as an internal color light-sensitive material with a multilayer construction, and more particularly, as a reversal color light-sensitive material or a negative color light-sensitive material.

The effects of the invention are most effectively exhibited when the light-sensitive material of the invention takes a layer construction comprising, in order, a support, a colloid silver antihalation layer, an intermediate layer, a red-sensitive layer, an intermediate layer, a green-sensitive layer, a colloid silver yellow filter layer, a blue-sensitive layer, and a protective layer. Each of the above-described red-sensitive, green-sensitive, and blue-sensitive layers may be divided into low-sensitive and high-sensitive layers. In addition, there can be employed, for example, a layer construction in which at least one of the red-sensitive, green-sensitive and blue-sensitive layers is divided into three layers, as described in Japanese patent publication No. 15495/74, a layer construction in which a high sensitive emulsion layer unit is separated from a low sensitive emulsion layer unit, as described in Japanese patent application (OPI) No. 49027/76, and layer constructions as described in West German patent application (OLS) Nos. 2,622,922, 2,622,923, 2,622,924, 2,704,826 and 2,704,797.

The present light-sensitive material is exposed to light by the usual procedures to obtain photographic images or patterns. For this exposure, a number of known light sources can be used, including natural light (sunlight), a tungsten lamp, a fluorescent lamp, a mercury lamp, a xenon arc lamp, a carbon arc lamp, a xenon flash lamp, and a cathode ray tube frying spot. The exposure time may be, of course, within the range of from $10^{-3}$ to 1 second, which is used in the ordinary camera, or may be shorter than $10^{-3}$ second, for example, within the range of from $10^{-4}$ to $10^{-6}$ second which is employed in using, for example, a xenon flash lamp and a cathode ray tube. Moreover, an exposure time longer than 1 second can be used. If necessary, the spectral composition of the light for use in exposure can be regulated by means of a color filter. Laser light can be used in exposing the light-sensitive material. In addition, the light emitted from a fluorescent body excited by electron ray, X-ray, $\gamma$-ray, $\alpha$-ray, or the like can be used.

In photographic processing of the light-sensitive material of the invention, any of the known methods can be used, and known processing solutions can be used. The processing temperature is usually from 18° to 50° C., but may be higher than 50° C. or lower than 18° C. Either of a development processing (black-and-white photographic development) to form a silver image and a color photographic processing including a development processing to form a dye image can be applied optionally.

Developers for use in the black-and-white photographic processing can contain known developing agents, such as dihydroxybenzenes (e.g., hydroquinones), 3-pyrazolidones (e.g., 1-phenyl-3-pyrazolidone), aminophenols (e.g., N-methyl-p-aminophenol), 1-phenyl-3-pyrazolines, ascorbic acid, and heterocyclic compounds described in U.S. Pat. No. 4,067,872, which are similar in structure to the condensate of a 1,2,3,4-tetrahydroquinoline ring and an indolenine ring. These compounds can be used alone or in combination with each other. In general, the developers may contain other known additives, such as a preservative, an alkali agent, a pH buffer, and an antifoggant, and if desired, a dissolving aid, a color controller, a development accelerator, a surface active agent, a defoaming agent, a hard water-softener, a hardening agent, a tackifier, and so forth.

The so-called lith type development can be applied to the photographic emulsion as used herein. The lith type development is a process in which for photographic reproduction of line images or of half-tone images in terms of dots dihydroxybenzenes are usually used as developing agents and the development is infectiously performed at a low sulfite ion concentration. (This process is described in detail in Mason, *Photographic Processing Chemistry*, pp. 163-165 (1966).)

As a special type of development, there may be used a process in which a developing agent is incorporated into a light-sensitive material, for example, an emulsion layer, and the resulting light-sensitive material is processed in an alkaline aqueous solution to achieve development. Hydrophobic ones of the developing agents, as disclosed in *Research Disclosure*, No. 169, RD-16928, can be incorporated into the emulsion layer, previously dispersed in a latex. This type of development processing may be performed in combination with a silver salt stabilization processing using thiocyanic acid salts.

Conventionally used fixers can be used in the invention. As fixing agents, in addition to thiosulfates and thiocyanic acid salts, organosulfurous compounds which are known to be effective as fixing agents can be used. These fixers may contain water-soluble aluminum salts as hardening agents.

In forming dye images, the usual procedures can be employed, including a negative-positive process (as described in, for example, *Journal of the Society of Motion Picture and Television Engineers*, Vol. 61, pp. 667-701 (1953)), a color reversal process in which a negative silver image is formed by developing with a developer containing a black-and-white developing agent, is uniformly exposed to light or subjected to a suitable fogging treatment at least once, and subsequently, is color developed, and a silver dye bleaching process in which a photographic emulsion layer containing a dye is exposed and developed to form a silver image, and with the silver image as a bleaching catalyst, the dye is bleached.

A color developer is generally composed of an alkaline aqueous solution containing a color developing agent. As such color developing agents, known primary aromatic amine developing agents, such as phenylenediamines (e.g., 4-amino-N,N-diethylaniline, 3-methyl-4-amino-N,N-diethylaniline, 4-amino-N-ethyl-N-$\beta$-hydroxyethylaniline, 3-methyl-4-amino-N-ethyl-N-$\beta$-hydroxyethylaniline, 3-methyl-4-amino-N-ethyl-N-$\beta$-methanesulfonamidoethylaniline, and 4-amino-3-methyl-N-ethyl-N-$\beta$-methoxyethylaniline) can be used.

In addition, it is possible to use those compounds described in, for example, L. F. A. Mason, *Photographic Processing Chemistry*, Focal Press Co., (1966), pp. 226-229, U.S. Pat. Nos. 2,193,015 and 2,592,364, and Japanese patent application (OPI) No. 64933/73.

These color developers can further contain pH buffers, such as the sulfurous acid salts, carbonic acid salts, boric acid salts, and phosphoric acid salts of alkali metals, development inhibitors, such as bromides, iodides, and organic antifoggants, antifoggants, and so forth. If necessary, they may contain a hard water-softening agent, a preservative, e.g., hydroxyamine, an organic solvent, e.g., benzyl alcohol and diethylene glycol, a development accelerator, e.g., polyethylene glycol, quaternary ammonium salts, and amines, a dyeforming coupler, a competitive coupler, a fogging agent, e.g., sodium borohydride, an auxiliary developer, e.g., 1-phenyl-3-pyrazolidone, a tackifier, a polycarboxylic acid-based chelating agent as described in U.S. Pat. No. 4,083,723 and an antioxidant as described in West German patent application (OLS) No. 2,622,950.

After color development, the photographic emulsion layer is usually bleached. This bleaching processing may be performed concurrently with a fixing processing or separately. Bleaching agents which can be used include multivalent metal (iron (III), cobalt (III), chromium (VI), copper (II), etc.) compounds, peracids, quinones, and nitroso compounds. For example, ferricyanides, dichromic acid salts, organic complex salts of iron (III) or cobalt (III), aminopolycarboxylic acids, e.g., ethylenediaminetetraacetic acid, nitrilotriacetic acid, and 1,3-diamino-2-propanoltetraacetic acid, complex salts of organic acids, such as citric acid, tartaric acid, and malic acid, persulfuric acid salts, permanganic acid salts, and nitrosophenol can be used.

In the light-sensitive material of the invention, the desilvering rate is high particularly when it is processed with bleaching agents having a low bleaching power, e.g., persulfuric acid salts. It is, therefore, preferred to process the present light-sensitive material with such bleaching agents causing no pollution.

Bleaching or bleach-fixing solutions can contain bleach-accelerators as described in, for example, U.S. Pat. Nos. 3,042,520 and 3,241,966, and Japanese patent publication Nos. 8506/70 and 8836/70, thiol compounds as described in Japanese patent application (OPI) No. 65732/78, and other various additives.

When bleaching agents having a low bleaching power, e.g., persulfates, are used, bleach-accelerators may be incorporated into a bleaching solution, a bleach-fixing solution, or its pre-bath. Examples of useful bleach-accelerators include those compounds described in U.S. Pat. Nos. 3,772,020, 3,893,858, 3,707,374, Japanese patent publication No. 28227/76, Japanese patent application (OPI) No. 26506/80, and *Research Disclosure*, No. 15704.

The following examples are given to illustrate the invention in greater detail.

EXAMPLE 1

A multilayer color light-sensitive material was prepared by providing the layers as described below on a cellulose triacetate film support.

Layer 1 Antihalation Layer:

To 1 kg of a black colloid silver emulsion (containing 15 g of blacked silver and 100 g of gelatin per 1 kg of the emulsion) was added 40 ml of a 5% by weight aqueous solution of a coating agent, sodium p-dodecylbenzenesulfonate, and the resulting mixture was coated in a dry film thickness of $2\mu$.

Layer 2 Gelatin Intermediate Layer (dry film thickness: $1.0\mu$)

Layer 3 Red-Sensitive Low Sensitivity Silver Halide Emulsion Layer:

A silver iodobromide emulsion (mean grain size: $0.3\mu$; containing 100 g of silver halide and 70 g of gelatin per 1 kg of the emulsion) containing 5 mol% of iodine was prepared in the usual manner. To 1 kg of the emulsion were added 210 ml of a 0.1% methanol solution of anhydro-5,5-dichloro-9-ethyl-3,3'-di(3-sulfopropyl)thiacarbocyaninehydroxide pyridinium sulfide, as a red-sensitive spectral sensitizing agent, and then 20 ml of a 5% by weight aqueous solution of 5-methyl-7-hydroxy-2,3,4-triazaindolizine, 400 g of Cyan Coupler Emulsion (I) and 200 g of Emulsion (II), each emulsion having the composition as described hereinafter. Then, 200 ml of a 2% aqueous solution of Colored Cyan Coupler (CC-1) was added, and further, 30 ml of a 2% by weight aqueous solution of a 2-hydroxy-4,6-dichlorotriazine sodium salt as a gelatin hardening agent was added to prepare a red-sensitive low sensitivity silver halide emulsion. This emulsion was coated in a dry film thickness of $3.5\mu$.

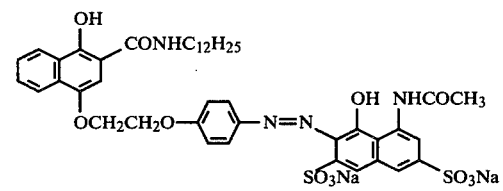

CC-1

Emulsion (I)
10% by weight aqueous solution of gelatin: 1,000 g
Sodium p-dodecylbenzenesulfonate: 5 g
Tricresyl phosphate: 60 ml
Cyan Coupler (C-101): 70 g
Ethyl acetate: 100 ml Sodium p-dodecylbenzenesulfonate, tricresyl phosphate, Cyan Coupler (C-101) and ethyl acetate were mixed and dissolved at 55° C., and the resulting solution was added to a 10% by weight solution of gelatin which had been heated to 55° C. and emulsified therein by means of a colloid mill.

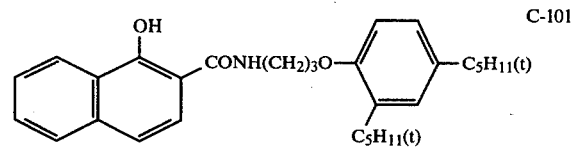

C-101

Emulsion (II)
10% by weight aqueous solution of gelatin: 1,000 g,
Sodium p-dodecylbenzenesulfonate: 5 g,
Tricresyl phosphate: 60 ml,
Cyan Coupler (C-101): 70 g,
DIR Compound (D-1): 10 g,
Ethyl acetate: 100 ml.

Sodium p-dodecylbenzenesulfonate, tricresyl phosphate, Cyan Coupler (C-101), DIR Compound (D-1), and ethyl acetate were mixed and dissolved at 55° C., and the resulting solution was added to a 10% by weight aqueous solution of gelatin which had been heated to 55° C. and emulsified therein by means of a colloid mill.

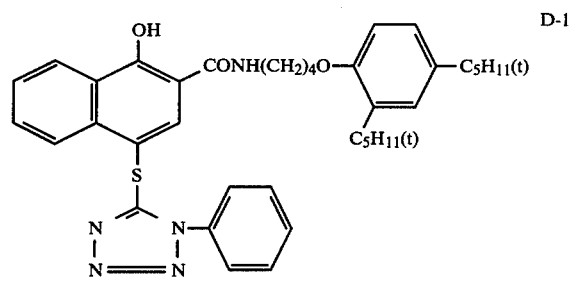

D-1

Layer 4 Red-Sensitive High Sensitivity Silver Halide Emulsion Layer:

A silver halide solution was prepared in the same manner as used in the preparation of the silver halide emulsion for Layer 3 except that the mean grain size of the emulsion was $0.9\mu$, and that the amounts of the red-sensitive spectral sensitizing agent, Emulsion (I), and Emulsion (II) added were 140 ml, 220 g, and 30 g, respectively.

The thus-prepared silver halide solution was coated in a dry film thickness of $2.2\mu$.

Layer 5 Gelatin Intermediate Layer (dry film thickness: $0.8\mu$)

Layer 6 Green-Sensitive Low Sensitivity Silver Halide Emulsion Layer:

To 1 kg of the same silver iodobromide emulsion as used in the preparation of Layer 3 were successively added as green-sensitive spectral sensitizing agent 180 ml of a 0.1% methanol solution of 3,3-di(2-sulfoethyl)-9-ethylbenzoxacarbocyanine pyridinium salt and 20 ml of a 5% by weight aqueous solution of 5-methyl-7-hydroxy-2,3,4-triazaindolizine, and then 320 g of Magenta Coupler Emulsion (III) and 180 g of Emulsion (IV). Further, 50 ml of a 2% by weight aqueous solution of 2-hydroxy-4,6-dichlorotriazine sodium salt as a gelatin hardening agent was added to prepare a green-sensitive low sensitivity silver halide emulsion. This emulsion was coated in a dry film thickness of 3.2μ.

Layer 7 Green-Sensitive High Sensitivity Silver Halide Emulsion Layer:

A silver halide solution was prepared in the same manner as in the preparation of the silver halide emulsion for Layer 6 except that the mean grain size of the emulsion was 1.0μ, the iodine content of the emulsion was 6.5 mol%, and that the amounts of the green-sensitive spectral sensitizing agent, Emulsion (III), and Emulsion (IV) added were 100 ml, 150 g, and 30 g, respectively.

The thus-prepared silver halide solution was coated in a dry film thickness of 2.2μ.

Emulsion (III)
  10% by weight aqueous solution of gelatin: 1,000 g,
  Sodium p-dodecylbenzenesulfonate: 5 g,
  Tricresyl phosphate: 80 ml,
  Magenta Coupler (M-101): 50 g,
  Colored Magenta Coupler (CM-1): 10 g,
  Ethyl acetate: 120 ml.

Sodium p-dodecylbenzenesulfonate, tricresyl phosphate, Magenta Coupler (M-101), Colored Magenta Coupler (CM-1), and ethyl acetate were mixed and dissolved at 55° C., and the resulting solution was added to a 10% by weight aqueous solution of gelatin which had been heated to 55° C. and emulsified therein by means of a colloid mill.

55° C., and emulsified therein by means of a colloid mill.

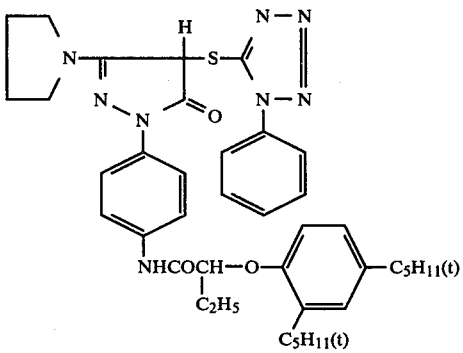

D-2

Layer 8 Yellow Filter Layer:

To 1 kg of a yellow colloid silver emulsion (containing 8.9 g of colloid silver and 67 g of gelatin per kg of the emulsion) was added 100 ml of a 5% by weight aqueous solution of sodium p-dodecylbenzenesulfonate as a coating agent. The resulting mixture was then coated in a dry film thickness of 1.6μ. The amount of silver (Ag) coated was 50 mg/m².

Layer 9 Blue-Sensitive Low Sensitivity Silver Halide Emulsion Layer:

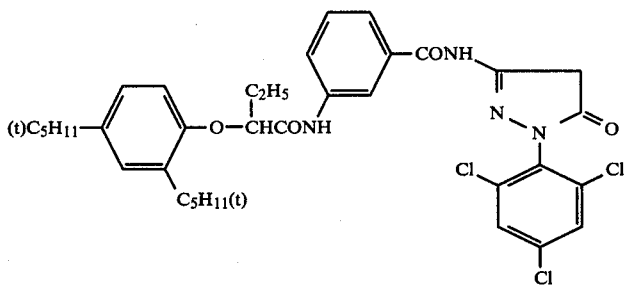

M-101

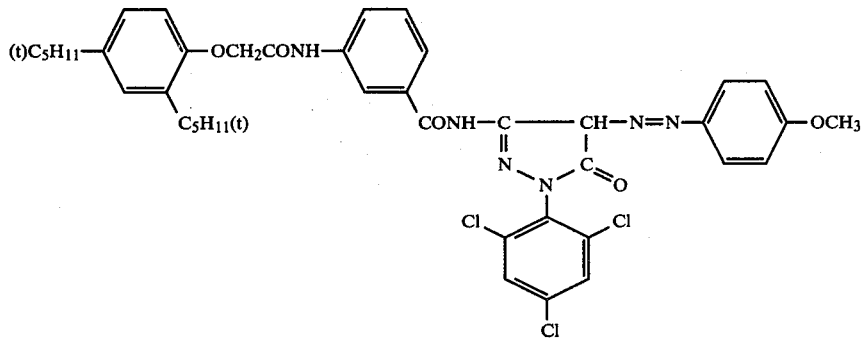

CM-1

Emulsion (IV)
  10% by weight aqueous solution of gelatin: 1,000 g,
  Sodium p-dodecylbenzenesulfonate: 5 g,
  Tricresyl phosphate: 80 ml,
  Magenta Coupler (M-101): 50 g,
  Colored Magenta Coupler (CM-1): 10 g,
  DIR Compound (D-2): 15 g,
  Ethyl acetate: 120 ml.

A mixture of sodium p-dodecylbenzenesulfonate, tricresyl phosphate, Magenta Coupler (M-101), Colored Magenta Coupler (CM-1), DIR Compound (D-2), and ethyl acetate was dissolved at 55° C., added to a 10% aqueous solution of gelatin which had been heated to To 1 kg of the same silver iodobromide emulsion as used in the preparation of Layer 3 with the exception that the mean grain size was 0.5μ were added 20 ml of a 5% by weight aqueous solution of 5-methyl-7-hydroxy-2,3,4-triazaindolizine and 1,500 g of Yellow Coupler Emulsion (V), the composition being described hereinafter. Further, 50 ml of a 2% by weight aqueous solution of 2-hydroxy-4,6-dichlorotriazine sodium salt as a gelatin hardening agent was added to prepare a blue-sensitive low sensitivity silver halide emulsion.

The thus-prepared emulsion was coated in a dry film thickness of 3.0μ.

Emulsion (V)

10% by weight aqueous solution of gelatin: 1,000 g,
Sodium p-dodecylbenzenesulfonate: 5 g,
Tricresyl phospha
Ethyl acetate: 120 m.

A mixture of sodium p-dodecylbenzenesulfonate, tricresyl phosphate, Yellow Coupler (Y-1), and ethyl acetate was dissolved at 55° C., added to a 10% by weight aqueous solution of gelatin which had been heated to 55° C., and emulsified therein by means of a colloid mill.

Layer 10 Blue-Sensitive High Sensitivity Silver Halide Emulsion Layer:

A silver halide solution was prepared in the same manner as in the preparation of the silver halide emulsion for Layer 9 except that the mean grain size of the emulsion was 1:1μ and the amount of Emulsion (V) was 300 g.

The thus-prepared silver halide solution was coated in a dry film thickness of 2.5μ.

Layer 11 Gelatin Protective Layer (dry film thickness: 1.5μ)

The thus-prepared sample is designated as Film A.

Into the yellow filter layer of Film A were incorporated, as shown in Table 1, 1-phenyl-5-mercaptotetrazole and Compounds (2) to (5) (methanol solutions), each being $2.1 \times 10^{-2}$ mol per mol of colloid silver, to prepare Films B to F.

The above-prepared samples, Films A to F, were subjected to a forced film storage testing for the purpose of observing changes naturally appearing over a long period of time in a short period of time.

This forced film storage testing was performed under the following conditions:

Condition I: stored at room temperature for 3 days
Condition II: stored at 50° C. and 60% RH for 3 days
Condition III: stored at 45° C. and 80% RH for 3 days.

After this forced film storage testing, each film was exposed wedgewise to light and processed as described hereinafter. The characteristic curve of the green-sensitive layer adjacent to the yellow filter layer was obtained by an automatic density measurement, and on the basis of the curve, the minimum density $D_{min}$ and the relative logarithmic sensitivity $S_{0.2}$ (as measured by an exposure amount providing a density of fog+0.2) of the green-sensitive layer were determined. The results are shown in Table 1.

| Processing Steps | Temperature (°C.) | Time (min) |
|---|---|---|
| Color Development | 41 | 3 |
| Stopping | 38 | 0.5 |
| Water-Washing | " | " |
| Desilvering Accelerating Bath | " | " |
| Bleaching | " | 3 |
| Water-Washing | " | 1 |
| Fixing | " | 2 |
| Water-Washing | " | 2 |
| Stabilizing Bath | " | 1/6 |

The composition of each processing solution was as follows:

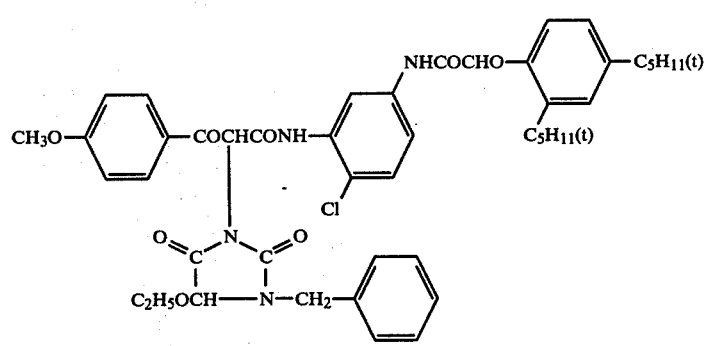

Y-1

| Color Devoloper | |
|---|---|
| Sodium hydroxide | 2 g |
| Sodium sulfite | 2 g |
| Potassium bromide | 1.4 g |
| Sodium chloride | 1 g |
| Borax | 1 g |
| Hydroxyamine sulfate | 4 g |
| Disodium ethylenediaminetetraacetate | 2 g |
| 4-Amino-3-methyl-N—ethyl-N—(β-hydroxyethyl)aniline monosulfate | 4 g |
| Water to make | 1 liter |
| Stop Solution | |
| Water | 800 ml |
| Glacial acetic acid | 30.0 ml |
| Caustic soda | 1.65 g |
| Water to make | 1 liter |
| Bleach Accelerator | |
| Sodium sulfite (anhydrous) | 9.0 g |
| 2—N,N—Diethylaminoethylisothiourea-3-dihydrochloride | 2.5 g |
| Sodium acetate | 8.0 g |
| Glacial acetic acid | 2.3 ml |
| Water to make | 1 liter |
| Bleaching Solution | |
| Sodium persulfate | 60 g |
| Sodium chloride | 20 g |
| Sodium dihydrophosphate | 15 g |
| Sodium tetrapolyphosphate | 2 g |
| β-Alanine | 2 g |
| Phosphoric acid (85%) | 2.2 ml |
| Water to make | 1 liter |
| Fixer | |
| Sodium thiosulfate | 150 g |
| Sodium sulfite (anhydrous) | 15 g |
| Borax | 12 g |
| Glacial acetic acid | 15 ml |
| Water to make | 1 liter |
| Stabilizing Bath | |
| Formaldehyde (37%) | 10 ml |
| Water to make | 1 liter |

TABLE 1

| Film | Type of Antifoggant | Green-Sensitive Layer $D_{min}$ | | | Green-Sensitive Layer $S_{0.2}$ | | |
|---|---|---|---|---|---|---|---|
| | | Condition I | Condition II | Condition III | Condition I | Condition II | Condition III |
| A | Blank | 0.60 | 0.59 | 0.68 | −2.23 | −2.26 | −2.05 |
| B | 1-Phenyl-5-mercaptotetrazole | 0.56 | 0.55 | 0.63 | −2.20 | −2.22 | −2.03 |
| C | Compound (2) | 0.55 | 0.54 | 0.57 | −2.21 | −2.20 | −2.08 |
| D | Compound (3) | 0.55 | 0.54 | 0.58 | −2.22 | −2.22 | −2.08 |
| E | Compound (4) | 0.55 | 0.54 | 0.59 | −2.22 | −2.23 | −2.10 |
| F | Compound (5) | 0.55 | 0.54 | 0.59 | −2.22 | −2.21 | −2.09 |

In order to examine the desilvering rate of yellow colloid silver in each of Films A to F, the minimum yellow color density when the above-described bleach processing was performed for 1 minute or 3 minutes was determined. The results are shown in Table 2.

TABLE 2

| Film | Type of Antifoggant | Minimum Yellow Color Density | |
|---|---|---|---|
| | | Bleached for 1 Minute | Bleached for 3 Minutes |
| A | Blank | 1.04 | 1.04 |
| B | 1-Phenyl-5-mercaptotetrazole | 1.06 | 1.04 |
| C | Compound (2) | 1.01 | 0.99 |
| D | Compound (3) | 1.01 | 1.01 |
| E | Compound (4) | 1.02 | 1.01 |
| F | Compound (5) | 1.03 | 1.01 |

It is apparent from Tables 1 and 2 that the use of Compound (2), (3), (4) or (5) of the invention retards the increase in fog of the adjacent layer due to the presence of colloid silver and reduces the magnitude of variation in sensitivity. In particular, the fog-preventing effect under Forced Storage Test Condition (III) (wet conditions) is prominent. Thus, when the antifoggants of the invention are used, changes in fog with a lapse of time are reduced, resulting in reduced variation in photographic sensitivity, and there can be obtained desirable photographs.

Some of the compounds showing the fog-preventing action form stable silver salts, deteriorating desilvering properties. In the case of such compounds, when a bleach processing is performed using, for example, persulfates having a low bleaching power, it is inevitably necessary to minimize the amounts of the compounds used because of their desilvering inhibiting properties. As apparent from Table 2, when the antifoggants are used in an amount effective for allowing them to exhibit the fog-preventing action, 1-phenyl-5-mercaptotetrazole provides a high yellow density resulting from poor desilvering, whereas the compounds of the invention have almost no desilvering inhibiting properties (i.e., poor desilvering of yellow colloid silver). It is believed, therefore, that the present compounds are very effective antifoggants in the bleach processing of low bleaching power. It is due to the fog-preventing effect of the compounds of the invention that in Table 2 Films C to F are lower than in yellow density than Film A.

Even when the compounds of the invention are incorporated into the antihalation layer in which colloid silver is used, the same fog-preventing effect as incorporated into the yellow filter layer can be obtained.

EXAMPLE 2

A coated sample was prepared by providing the following two layers, in order, on a cellulose triacetate film support coated with the usual subbing layer. This is designated as Film G.

Layer 1 Silver Halide Emulsion Layer:

A silver iodobromide emulsion (mean grain size: 1.2μ; containing 100 g of silver halide and 70 g of gelatin per kg of the emulsion) containing 6.5 mol% of iodine was prepared by the usual procedure. To 1 kg of the emulsion were added 20 ml of a 5% by weight aqueous solution of 5-methyl-7-hydroxy-2,3,4-triazaindolizine, 500 g of a Magenta Coupler Emulsion, the composition being described hereinafter, and further, 30 ml of a 2% by weight aqueous solution of 2-hydroxy-4,6-dichlorotriazine sodium salt as a gelatin hardening agent to prepare a silver halide emulsion. The emulsion was coated in a dry film thickness of 5.0μ.

| Magenta Coupler Emulsion | |
|---|---|
| 10% by weight aqueous solution of gelatin | 1,000 g |
| Sodium p-dodecylbenzenesulfonate | 5 g |
| Tricresyl phosphate | 80 ml |
| Magenta Coupler (M-101 used in Example 1) | 50 g |
| Ethyl acetate | 100 ml |

A mixture of sodium p-dodecylbenzenesulfonate, tricresyl phosphate, Magenta Coupler (M-101), and ethyl acetate was dissolved at 55° C., added to a 10% by weight aqueous solution of gelatin which had been heated to 55° C., and then emulsified therein by means of a colloid mill.

Layer 2 Gelatin Protective Layer (dry film thickness: 1.5μ)

Into the silver halide emulsion layer of Film G was incorporated, as shown in Table 3, $0.3 \times 10^{-4}$ mol or $1 \times 10^{-4}$ mol of 1-phenyl-mercaptotetrazole and Compounds (2) and (4) (methanol solution) to prepare Films H to M.

The thus-prepared films were subjected to the same forced film storage testing as in Example 1.

This forced film storage testing was performed under the following conditions:

Condition I: stored at room temperature for 3 days
Condition II: stored at 50° C. and 60% RH for 3 days
Condition III: stored at 45° C. and 80% RH for 3 days After this forced film storage testing, each film was exposed wedgewise to light and processed as described hereinafter. The magenta color density was measured by an automatic densitometer, on basis of which the fog density and the relative logarithmic sensitivity $S_{0.2}$ (as measured by an exposure amount providing a density of fog + 0.2) were determined. The results are shown in Table 3.

| Processing Steps | Time (min) | Temperature (°C.) |
|---|---|---|
| Color Development | 3.25 | 38 |
| Bleaching | 6.5 | " |
| Water-Washing | 3.25 | " |
| Fixing | 6.5 | " |
| Water-Washing | 3.25 | " |
| Stabilizing | 3.25 | " |

The composition of each processing solution is as follows:

| Color Developer | |
|---|---|
| Sodium nitilotriacetate | 1.0 g |
| Sodium sulfite | 4.0 g |
| Sodium carbonate | 30.0 g |
| Potassium bromide | 1.4 g |
| Hydroxyamine sulfate | 2.4 g |
| 4-(N—Ethyl-N—β-hydroxyethylamino) 2-methylaniline sulfate | 4.5 g |
| Water to make | 1 liter |
| Bleaching Solution | |
| Ammonium bromide | 160.0 ml |
| Ammonia water (28%) | 25.0 ml |
| Sodium iron ethylenediaminetetraacetate | 130 g |
| Glacial acetic acid | 14 ml |
| Water to make | 1 liter |
| Fixer | |
| Sodium tetrapolyphosphate | 2.0 g |
| Sodium sulfite | 4.0 g |
| Ammonium thiosulfate (70%) | 175.0 ml |
| Sodium hydrogensulfate | 4.6 g |
| Water to make | 1 liter |
| Stabilizing Solution | |
| Formalin | 8.0 ml |
| Water to make | 1 liter |

TABLE 3

| Film | Type of Antifoggant | Amount (mol/silver halide mol) | Fog Density | | | $S_{0.2}$ | | |
|---|---|---|---|---|---|---|---|---|
| | | | Storage Condition I | Storage Condition II | Storage Condition III | Storage Condition I | Storage Condition II | Storage Condition III |
| G | Blank | 0 | 0.22 | 0.20 | 0.32 | −1.93 | −1.87 | −1.20 |
| H | 1-Phenyl-5-mercapto-tetrazole | $0.3 \times 10^{-4}$ | 0.19 | 0.17 | 0.30 | −1.94 | −1.87 | −1.21 |
| I | 1-Phenyl-5-mercapto-tetrazole | $1.0 \times 10^{-4}$ | 0.16 | 0.16 | 0.29 | −1.89 | −1.84 | −120 |
| J | Compound (2) | $0.3 \times 10^{-4}$ | 0.16 | 0.14 | 0.25 | −1.99 | −1.94 | −1.35 |
| K | Compound (2) | $1.0 \times 10^{-4}$ | 0.12 | 0.11 | 0.20 | −2.08 | −2.05 | −1.45 |
| L | Compound (4) | $0.3 \times 10^{-4}$ | 0.17 | 0.17 | 0.27 | −1.97 | −1.91 | −1.32 |
| M | Compound (4) | $1.0 \times 10^{-4}$ | 0.13 | 0.12 | 0.23 | −2.05 | −2.01 | −1.42 |

As apparent from Table 3, the use of the compounds of the invention, Compounds (2) and (4), retards the fog of the emulsion layer and produces a great increase in sensitivity as in the incorporation thereof into the colloid silver layer. Furthermore, the magnitude of variation in sensitivity with a lapse of time is small, and the fog-preventing effect particularly under Condition (III) (wet conditions) is prominent. Thus, the incorporation of the antifoggants of the invention into the emulsion layer also produces very high photographic performance.

While the invention has been described in detail and with reference to specific embodiments thereof, it will be apparent to one skilled in the art that various changes and modifications can be made therein without departing from the spirit and scope thereof.

What is claimed is:

1. A silver halide photographic light-sensitive material, comprising:
    a support base;
    a silver halide emulsion layer positioned on the support base; and
    a compound represented by the general formula (I):

$$\underset{SM}{\overset{N=N}{\underset{N-N}{\bigg\rangle}}} \!\!-\!\! \bigcirc \!\!-\!\! NHC(O)N\overset{R^1}{\underset{R^2}{\diagdown}} \quad (I)$$

wherein M is hydrogen, an alkali metal atom, or a quaternary ammonium group, and $R^1$ and $R^2$ are each hydrogen, a substituted or unsubstituted aliphatic group, or a substituted or unsubstituted aromatic group, and may be the same or different and may combine together to form a ring.

2. A silver halide photographic light-sensitive material as claimed in claim 1, wherein the material is an internal color light-sensitive material comprised of a multilayer construction which includes a plurality of silver halide emulsion layers.

3. A silver halide photographic light-sensitive material as claimed in claim 1, wherein the material is a reversal color light-sensitive material.

4. A silver halide photographic light-sensitive material as claimed in claim 1, wherein the material is a negative color light-sensitive material.

5. A silver halide photographic light-sensitive material as claimed in claim 1, wherein the material has a multilayer construction and includes a colloid silver antihalation layer, an intermediate layer, a red-sensitive layer, an intermediate layer, a green-sensitive layer, a colloid silver yellow filter layer, a blue-sensitive layer, and a protective layer.

6. A silver halide photographic light-sensitive material as claimed in claim 5, wherein the red-sensitive, green-sensitive and blue-sensitive layers are comprised of a low sensitivity and a high sensitivity layer.

7. A silver halide photographic light-sensitive material as claimed in claim 6, wherein the compound of general formula (I) is present within the colloid silver antihalation layer.

8. A silver halide photographic light-sensitive material as claimed in claim 1, wherein the compound of general formula (I) is present in an amount of from $10^{-8}$ to $10^{-2}$ mol per mol of silver halide.

9. A silver halide photographic light-sensitive material as claimed in claim 8, wherein the compound of general formula (I) is present in an amount of from $10^{-6}$ to $10^{-3}$ mol per mol of silver halide.

10. A silver halide photographic light-sensitive material as claimed in claim 1, wherein $R^1$ and $R^2$ represent aryl groups containing from 6 to 20 carbon atoms.

11. A silver halide photographic light-sensitive material as claimed in claim 1, wherein at least one of $R^1$ and $R^2$ represents alkyl groups containing 1 to 6 carbon atoms.

12. A silver halide photographic light-sensitive material as claimed in claim 11, wherein at least one of $R^1$ and $R^2$ represents a methyl group, an ethyl group, an n-propyl group, an n-butyl group or an n-pentyl group.

* * * * *